United States Patent [19]

VandenBerg

[11] Patent Number: Plant 7,577

[45] Date of Patent: Jul. 2, 1991

[54] CHRYSANTHEMUM PLANT NAMED YELLOW BOALDI

[75] Inventor: Cornelis P. VandenBerg, Salinas, Calif.

[73] Assignee: Yoder Brothers, Inc., Barberton, Ohio

[21] Appl. No.: 409,636

[22] Filed: Sep. 18, 1989

[51] Int. Cl.[5] ..... A01H 5/00

[52] U.S. Cl. ..... Plt./78

[58] Field of Search ..... Plt./77, 78

[56] References Cited

U.S. PATENT DOCUMENTS

| | | | |
|---|---|---|---|
| P.P. 4,889 | 9/1982 | van der Knaap | Plt. 78 |
| P.P. 5,226 | 5/1984 | Duffett | Plt. 78 |
| P.P. 5,351 | 11/1984 | Duffett | Plt. 78 |
| P.P. 6,223 | 7/1988 | Hesse | Plt. 78 |
| P.P. 6,613 | 2/1989 | Duffett | Plt. 77 |
| 4,616,099 | 10/1986 | Sparkes | 47/58 |

OTHER PUBLICATIONS

Broertjes, et al., 1980, "A Mutant of a Mutant of a Mutant of a . . . Irradiation of Progressive Radiation-Induced Mutants in a Mutation Breeding Programme with *Chrysanthemum morifolium*", Euphytica 29 (1980): 525-530.

Gosling, S. ed., 1979, "The Chrysanthemum Manual", Nat. Chrysanthemum Soc., London, England, pp. 329-336.

Broertjes et al., 1978, "Application of Mutation Breeding Methods in the Improvement of Vegetatively Propagated Crops", Elseveir Pub. Co., N.Y., pp. 162-175.

Searle, et al., 1968, "Chrysanthemums the Year Round", Blandford Press, London, pp. 26-29, 320-327.

Broertjes, 1966, "Mutation Breeding of Chrysanthemums", Euphytica 15 (1966): 156-162.

Chan et al., 1966, "Chrysanthemum and Rose Mutations Induced by X-rays", Am. Soc. Hort. Sci., vol. 88 (1966): 613-620.

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Yellow Boaldi particularly characterized by its flat capitulum form; decorative capitulum type; yellow ray floret color; diameter across face of capitulum of up to 11 cm at maturity when grown as a pinched disbudded pot mum; uniform eight week photoperiodic flowering response to short days; medium plant height when grown as a pinched pot mum; recommended both as disbudded and spray pot mum; and spreading and prolific branching pattern.

3 Drawing Sheets

The present invention comprises a new and distinct cultivar of Chrysanthemum, botanically known as *Dendranthema grandiflora*, and referred to by the cultivar name Yellow Boaldi.

Yellow Boaldi, identified as 81-D11A23, is a product of a mutation induction program which had the objective of creating new Chrysanthemum cultivars that would expand the color range of an existing cultivar while retaining all other traits.

Yellow Boaldi was discovered and selected by Cornelis P. VandenBerg on May 18, 1987 in a controlled environment in Salinas, Calif. as one flowering plant within a flowering block established as rooted cuttings from stock plants which had been exposed as unrooted cuttings to an X-ray source of 2,000 rads. The irradiated parent was the cultivar Boaldi, disclosed in U.S. Plant Pat. No. 6,613.

The first act of asexual reproduction of Yellow Boaldi was accomplished when vegetative cuttings were taken from the initial selection in July of 1987 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Yellow Boaldi are firmly fixed and are retained through successive generations of asexual reproduction.

Yellow Boaldi has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Yellow Boaldi, which, in combination, distinguish this Chrysanthemum as a new and distinct cultivar:

1. Flat capitulum form.
2. Decorative capitulum type.
3. Yellow ray floret color.
4. Diameter across face of capitulum of up to 11 cm at maturity, when grown as a pinched disbudded pot mum.
5. Uniform eight week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Recommended both as disbudded and spray pot mum.
8. Spreading and prolific branching pattern.

The accompanying photographic drawings show typical inflorescence and leaf characteristics of Yellow Boaldi, with the colors being as nearly true as possible with illustrations of this type.

Sheet 1 is a color photograph of Yellow Boaldi grown as a pinched disbudded pot mum.

Sheet 2 is a black and white photograph of three views of the inflorescence of Yellow Boaldi.

Sheet 3 is a black and white photograph showing the upper and under sides of the leaves of Yellow Boaldi at three stages of development (mature, intermediate and immature).

Of the commercial cultivars known to the inventor, the most similar in comparison to Yellow Boaldi is the parent cultivar Boaldi. All traits of Yellow Boaldi are similar to those of Boaldi, except the color of the ray florets. The color of the ray florets of Yellow Boaldi is yellow, as contrasted with the pure white ray florets of Boaldi.

In the following description, color references are made to The Royal Horticultural Society Colour Chart. The color values were determined on plant material grown as a pinched disbudded pot mum in Salinas, Calif. on June 8, 1989.

Classification:

*Botanical.*—*Dendranthema grandiflora* cv Yellow Boaldi.

*Commercial.*—Decorative disbud and spray pot mum.

INFLORESCENCE

A. Capitulum:

*Form.*—Flat.

*Type.*—Decorative.

*Diameter across face.*—Up to 11 cm at maturity when grown as a pinched disbudded pot mum.

B. Corolla of ray florets:

*Color general tonality from a distance of three meters).*—Yellow.

*Color (upper surface).*—4B to 4C, with center of flow closest to 4A.

*Color (under surface).*—4C.

*Shape.*—Flat, oblong.

C. Corolla of disc florets:

*Color (mature).*—Closest to 154B.

*Color (immature).*—Closest to 144B.

D. Reproductive organs:

*Androecium.*—Present on disc florets only; scant pollen.

*Gynoscium.*—Present on both ray and disc florets.

PLANT

A. General appearance:

*Height.*—Medium; 25 to 35 cm as a pinched pot mum with 0 to 7 long days after pinch prior to short days and 1 application of 2500 ppm B-9 SP.

*Branching pattern.*—Spreading and prolific.

B. Foliage:

*Color (upper surface).*—147A.

*Color (under surface).*—147B.

*Shape.*—Lobed and serrated.

I claim:

1. A new and distinct Chrysanthemum plant named Yellow Boaldi, as described and illustrated.

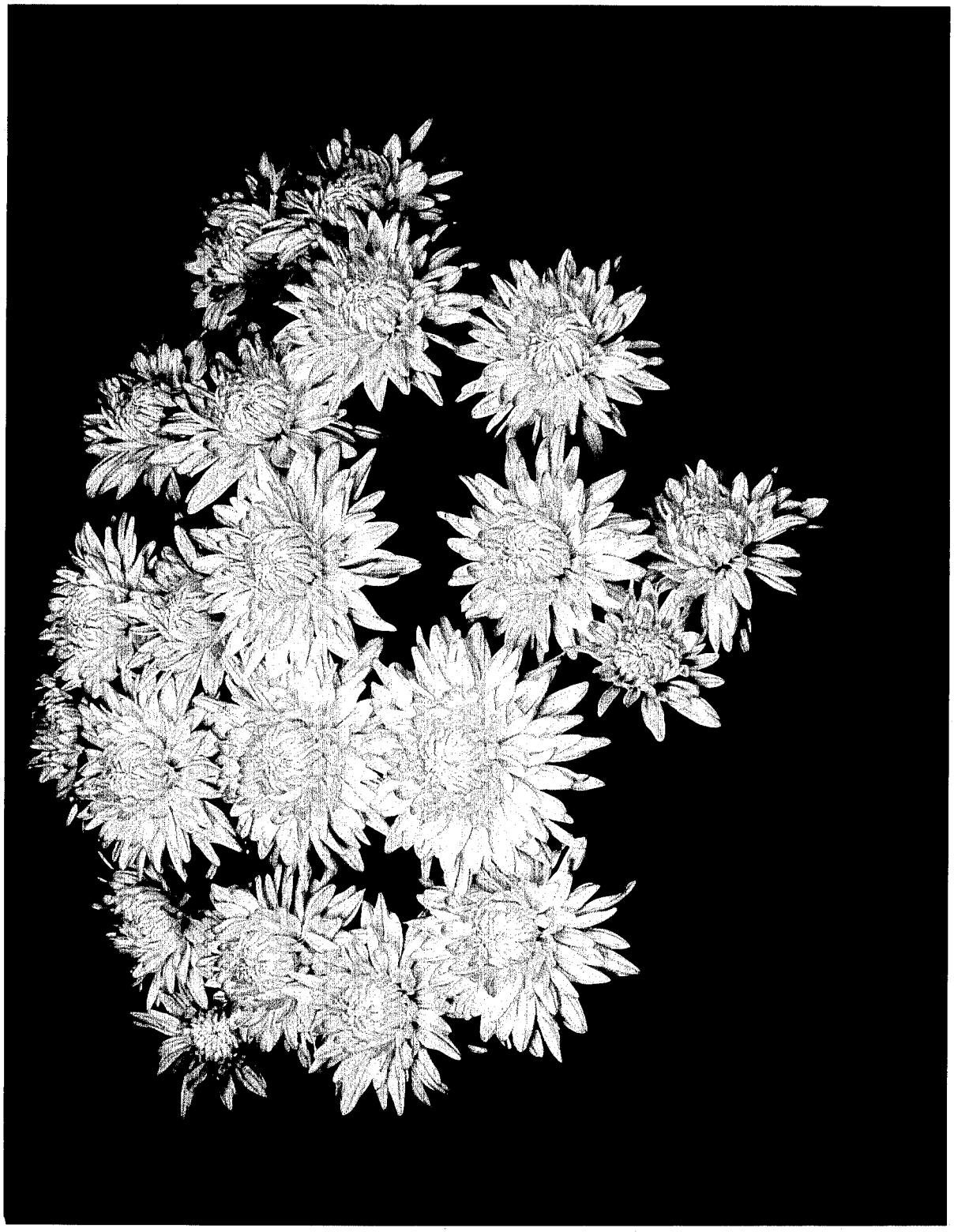

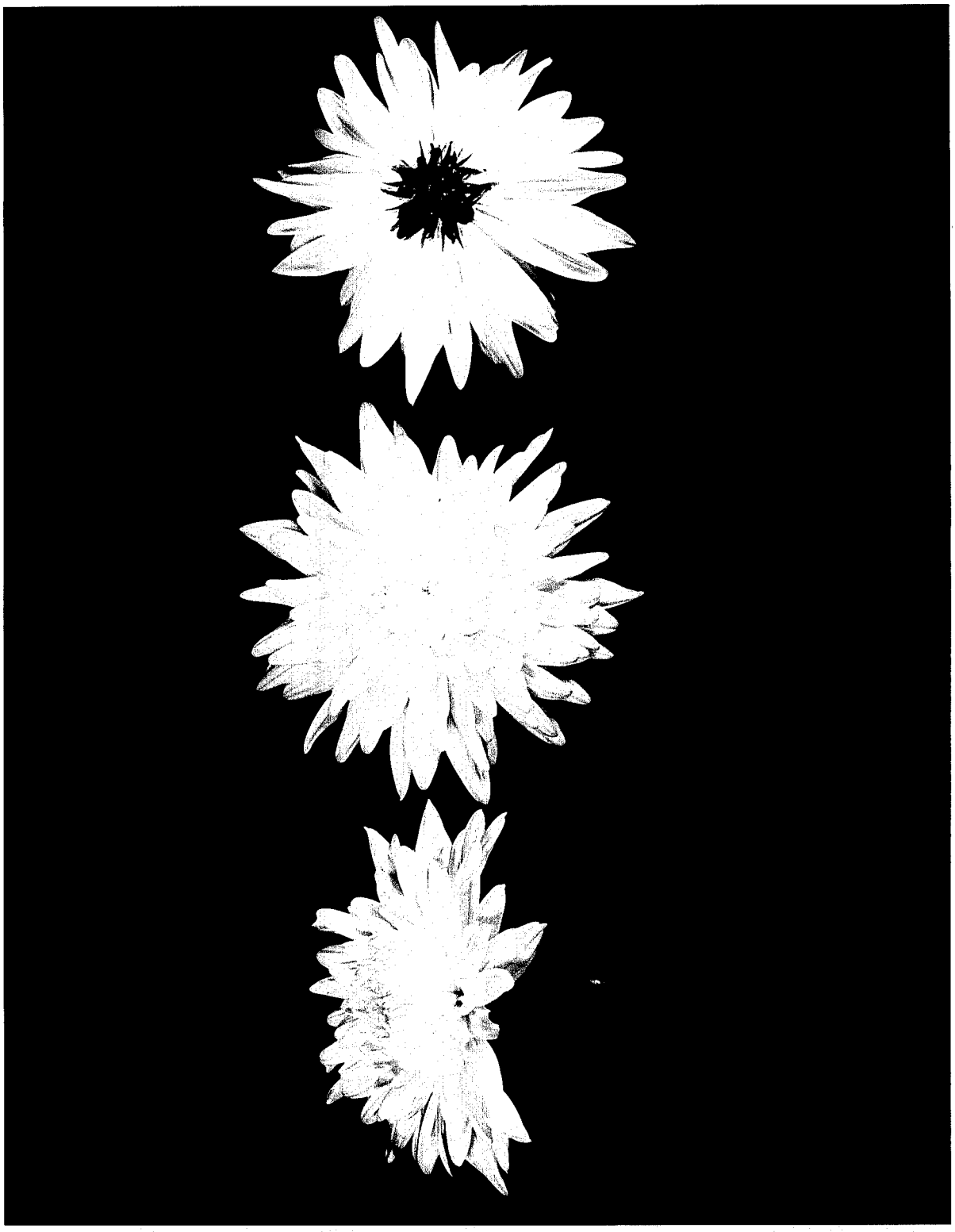

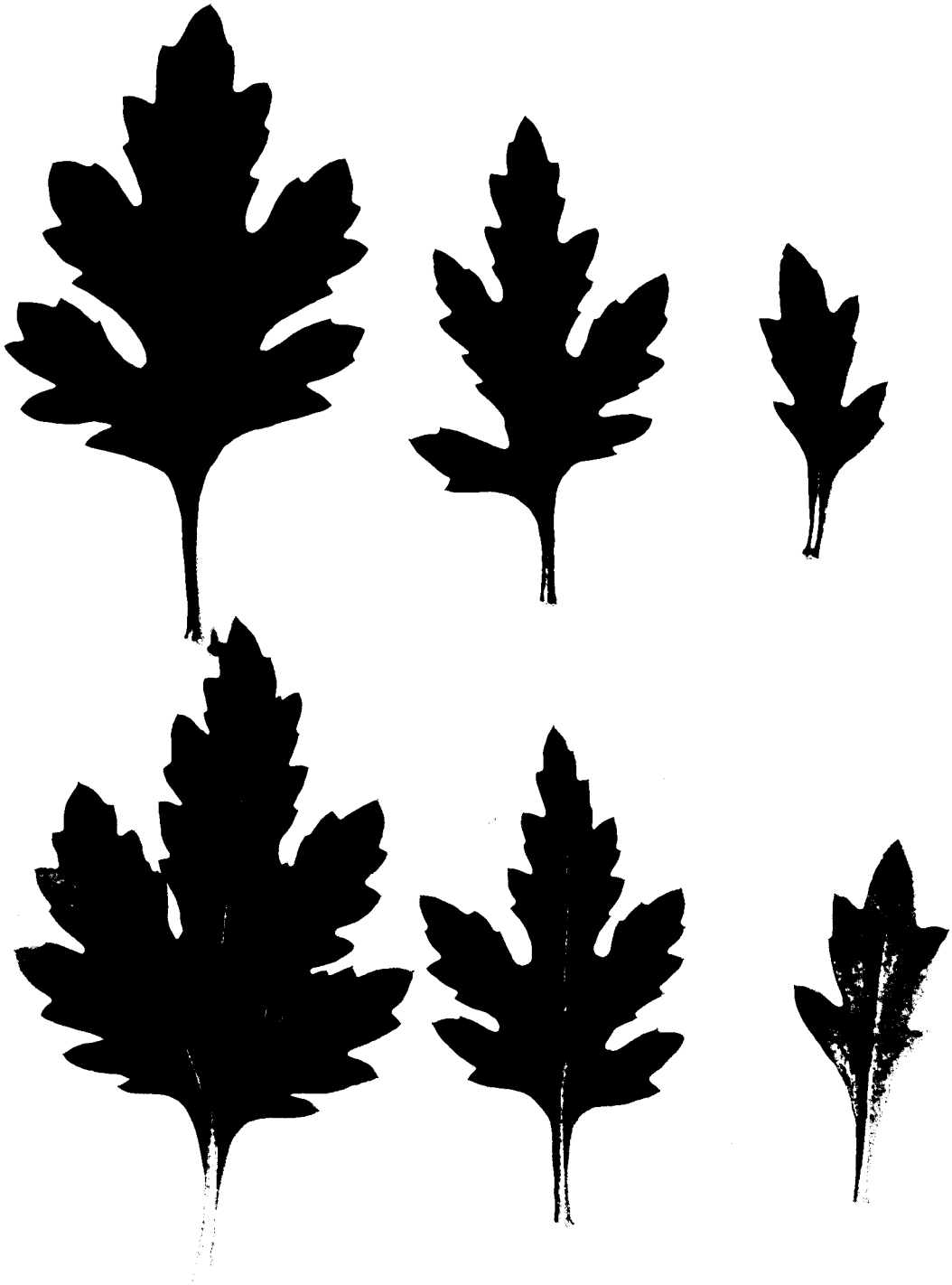

* * * * *